United States Patent [19]

Schmidt et al.

[11] Patent Number: 4,501,917

[45] Date of Patent: Feb. 26, 1985

[54] PROCESS FOR CARBONYLATING FORMALDEHYDE ACETALS

[75] Inventors: Hans-Joachim Schmidt, Königstein; Hans-Jürgen Arpe, Frankfurt am Main, both of Fed. Rep. of Germany

[73] Assignee: Hoechst Aktiengesellschaft, Frankfurt, Fed. Rep. of Germany

[21] Appl. No.: 405,429

[22] Filed: Aug. 5, 1982

[30] Foreign Application Priority Data

Aug. 7, 1981 [DE] Fed. Rep. of Germany ....... 3131355

[51] Int. Cl.$^3$ ............................................. C07C 69/66
[52] U.S. Cl. .................... 560/187; 560/114; 560/185; 560/60
[58] Field of Search .......................... 560/187, 60, 185

[56] References Cited

FOREIGN PATENT DOCUMENTS 1192178 5/1965 Fed. Rep. of Germany .
537980 7/1941 United Kingdom ................ 560/187

*Primary Examiner*—Paul J. Killos
*Attorney, Agent, or Firm*—Curtis, Morris & Safford

[57] ABSTRACT

The invention relates to a process for reacting RO—CH$_2$—OR formaldehyde acetals with carbon monoxide in the liquid phase on an acid organic ion exchange material as catalyst. The main products are ether-esters, RO—CH$_2$—COOR, of hydroxyacetic acid (glycolic acid).

8 Claims, No Drawings

PROCESS FOR CARBONYLATING FORMALDEHYDE ACETALS

The present invention relates to a process for reacting formaldehyde acetals of the general formula $$RO-CH_2-OR$$

in which the two R radicals can be identical or different and denote alkyl, alkoxyalkyl, cycloalkyl or phenylalkyl groups having up to 10 carbon atoms at elevated temperatures and pressures with carbon monoxide in the liquid phase.

The reaction according to the invention of formaldehyde acetals with carbon monoxide mainly produces ether-esters of hydroxyacetic acid (glycolic acid) according to a general equation (1) in which R has the above-mentioned meaning:

$$RO-CH_2-OR + CO \rightarrow RO-CH_2-COOR \quad (1)$$

The compounds of the formula $RO-CH_2-COOR$ are generally described below as "ether-esters of hydroxyacetic acid". In addition to these compounds, the reaction conditions can produce in small amounts by side reactions, for example hydrolysis, also esters of hydroxyacetic acid (glycolic acid) of the formula $HO-CH_2-COOR$ and those compounds which can formerly have been formed by ether elimination from two molecules of ether-esters of hydroxyacetic acid according to equation (2):

$$RO-CH_2COOR + RO-CH_2COOR \rightarrow RO-CH_2COOR-CH_2-COOR + R_2O \quad (2)$$

It is already known to react formaldehyde acetals with carbon monoxide in the presence of Lewis acid catalysts, such as boron trifluoride (U.S. Pat. No. 2,273,269) or hydrogen fluoride (U.S. Pat. No. 3,948,977) to form alkyl alkoxyacetates. However, these known processes require an uneconomically large excess of catalyst, for example 27–75 mole % of $BF_3$ or far above 100 mole % of HF, per mole of acetal used. However, to recover these catalysts, which are readily volatile in bulk and homogeneously dispersed in the reaction medium, is difficult and necessitates expensive measures.

It is also known, from German Offenlegungsschrift No. 2,617,085, to react aldehydes with carbon monoxide and water or alcohols or carboxylic acids in the presence of acid ion exchange materials to give hydroxycarboxylic acids or their esters or acyl derivatives (equations 3–5):

$$R-CHO + CO + H_2O \rightarrow HO-\underset{R}{\overset{|}{C}H}-COOH \quad (3)$$

$$R-CHO + CO + R^1OH \rightarrow HO-\underset{R}{\overset{|}{C}H}-COOR^1 \quad (4)$$

$$R-CHO + CO + R^2COOH \rightarrow R^2COO-\underset{R}{\overset{|}{C}H}-COOH \quad (5)$$

However, these processes only produce monoderivatives, ie. hydroxycarboxylic acids substituted either at the hydroxyl or at the carboxyl group.

It has now been found that formaldehyde acetals can be carbonylated in a simple manner to give ether-esters of hydroxyacetic acid when the reaction is carried out in the presence of acid organic ion exchange materials. The use of organic ion exchange materials as carbonylation catalyst has the great advantage that it is possible readily to separate off and re-use the catalyst or to carry out the reaction on a fixed catalyst in a continuous manner.

The invention therefore relates to a process for reacting formaldehyde acetals of the general formula $$RO-CH_2-OR$$

in which the two R radicals can be identical or different and denote alkyl, alkoxyalkyl, cycloalkyl or phenylalkyl groups having up to 10 carbon atoms at elevated temperatures and pressures with carbon monoxide in the liquid phase, which process comprises using as catalyst acid organic ion exchange materials having an exchange capacity of more than 0.5 mEq per g.

The observation, that acetals of formaldehyde can be carbonylated in the presence of acid organic ion exchange materials, was surprising, since it is known, for example from German Auslegeschrift No. 1,668,482, that, in acetals in the presence of acid ion exchange materials, the two acetal bonds are rendered very labile and thus, for example on reaction with nucleophilic reactants, the alkyl groups are readily eliminated with re-formation of the starting aldehydes. An analogous result had to be reckoned with in the case of the reaction according to the invention, namely the formation of formaldehyde, dialkyl ethers and other products, but it was not to be expected that carbon monoxide is incorporated in such a smooth way into the acetal molecule.

Formaldehyde acetals which can be reacted with carbon monoxide by the process according to the invention correspond to the general formula $RO-CH_2OR$ in which the two R radicals independently of one another denote alkyl, alkoxyalkyl, cycloalkyl or phenylalkyl groups having up to 10 carbon atoms. The dimethyl, diethyl, di-n-propyl, di-isobutyl, di-(2-ethoxyethyl), dicyclohexyl, dibenzyl and diphenylethyl acetals of formaldehyde and also mixed formaldehyde acetals, such as methylethyl formal or ethylpropyl formal, are particularly suitable.

Acid organic ion exchange materials used as catalysts according to the invention are commercially available cation exchange materials which are based on ringsulfonated copolymers of styrene or divinylbenzene or on perfluorosulfonated polymethylenes and have free sulfonic acid groups and exchange capacities of more than 0.5 mEq per gram. Strongly acid organic ion exchange materials having exchange capacities of more than 1 mEq per gram are preferable.

The water content of the ion exchange material can vary within wide limits. However, to avoid by-product formation by hydrolysis of the acetal used or the ether-ester of hydroxyacetic acid formed, it is advantageous to use ion exchange materials having a water content of less than 5% by weight. Ion exchange materials having a higher water content can be dewatered by known methods, for example by drying using heat or in vacuo, by washing with a hydrophilic solvent, such as isopropanol, acetic acid or acetone, by reaction with acetic anhydride and by azeotropic distillation, for example using benzene.

The formaldehyde acetals can be used undiluted or mixed with one or more solvents or diluents. Examples of materials suitable for this purpose are aliphatic and aromatic hydrocarbons, ethers, carboxylates and, if appropriate, also the carbonylation-produced ether-ester of hydroxyacetic acid itself.

The weight ratio of ion exchange materials to formaldehyde acetals can be varied within wide limits. Since the ion exchange materials used can be readily separated from the reaction mixture owing to their particle size and insolubility, while, on the other hand, the rate of reaction of the acetal increases with increasing ion exchange material concentration, it is advantageous to choose concentrations which are not too low. Ion exchange concentrations of more than 1% by weight, relative to the reaction solution used, ie. relative to the sum of the formal used and, if appropriate, solvent or diluent, are preferable.

The reaction mixture is generally worked up by distillation. If appropriate, the compounds formed according to equation (2) can be quantitatively split (by reacting the reaction mixture with an alcohol in the presence of the ion exchange material) into equimolar amounts of ether-ester of hydroxyacetic acid and glycolate before or during the distillation. An alcohol is advantageously used for this purpose which corresponds to the formaldehyde acetal used, for example methyl alcohol in the case of formaldehyde dimethylacetal. After this treatment the reaction mixture contains as carbonylation products only the simply separable glycolate and ether-ester mentioned.

To carry out the process according to the invention, the acetal is suitably brought into contact with carbon monoxide and the ion exchange material, for example in pressure vessels having a stirring, piston or shaking device or, in the case of continuous operation, advantageously in flow tubes containing fixed catalyst.

When working in pressure vessels, carbon monoxide is supplied to the reaction mixture in a customary way, for example from pressure cylinders or by means of a pump, if appropriate after flushing with nitrogen. As the reaction proceeds and the pressure drops in a corresponding manner, the carbon monoxide consumed can be replenished in the same way. When working in a continuous manner, acetal and carbon monoxide are continuously supplied to the reaction zone and a corresponding amount of reaction mixture and residual gas are removed.

In a preferable continuous embodiment of the process according to the invention, the ion exchange material is mounted as a solid or fluid bed in a flow tube and the acetal, if appropriate diluted with a solvent, and the carbon monoxide are passed through the ion exchange material bed, it being possible for the starting products to be metered in at different points of the ion exchange layer.

The reaction temperature generally is between 25° and 200° C., preferably between 50° and 180° C., but the upper temperature limit is determined by the type of the ion exchange material used. In the case of strongly acid ion exchange materials based on styrene/divinylbenzene copolymers, the upper temperature limit is, in general, 120°–140° C., being about 170°–180° C. in the case of perfluorosulfonated polymethylenes.

The pressures used for the reaction are between 10 and 300 bar, preferably between 50 and 250 bar. Pressure and temperature are so chosen that the acetal used, and, if present, the solvent or diluent, are present in the liquid phase under the reaction conditions.

After the reaction, the insoluble ion exchange material is separated off in a suitable way, for example by filtration or decanting, and the reaction products are isolated by fractional distillation.

The ether-esters of hydroxyacetic acid and glycolates are used in many different ways as intermediates and as solvents.

The invention is illustrated by the Examples which follow.

EXAMPLE 1

A 200 ml shaker autoclave was filled with 50 g of formaldehyde dimethylacetal (methylal) and 10 g of a commercially available macroreticular ion exchange resin in $H^+$ form (water content 1.2% by weight, exchange capacity 4.6 mEq/g). After flushing with nitrogen, a carbon monoxide pressure of 140 bar was established, and the autoclave was heated for 4 hours at 130° C. while being shaken. When the pressure decreased, the starting pressure was reestablished by adding fresh carbon monoxide. After the mixture had cooled down, an investigation of the reaction mixture by gas chromatography showed a methylal conversion of 95 mole % and a selectivity to methyl methoxyacetate of 53%, to methyl glycolate of 18.5% and to methyl methoxyacetylglycolate of 22.2%.

The reaction mixture was filtered, and the ion exchange material was washed twice with 10 g of methylal in each case. Distillation of the combined filtrates over an 80 cm packed column produced 50 g of methyl methoxyacetate of boiling point 130°–131°/1 bar, 14 g of methyl glycolate of boiling point 63°–64° C./28 mbar and 16 g of methyl methoxyacetylglycolate of boiling point 64°–65° C./0.13 mbar.

It was possible to use the ion exchange material recovered by filtration repeatedly for carbonylating methylal. After a total of five uses, the methylal conversion was still above 90% while the selectivities were virtually unchanged.

EXAMPLE 2

A 2 liter stirred autoclave was filled with 500 g of methylal, 500 g of methyl acetate and 50 g of the ion exchange material mentioned in Example 1. After flushing with nitrogen, carbon monoxide was added up to a pressure of 140 bar and the mixture was heated for 3 hours at 130° C. while stirring at a rate of 1,000 revolutions per minute. The reduction in pressure in the reaction was compensated for by adding fresh carbon monoxide. After cooling down and letting down, the reaction mixture contained 39.4% by weight of methyl methoxyacetate, 5.7% by weight of methyl glycolate and 7.0% by weight of methyl methoxyacetylglycolate in addition to methyl acetate and small amounts (about 2% by weight) of other products, such as acetic acid, dimethyl ether and methanol. The methylal conversion was 99%, and the selectivity to the CO-insertion products was, in total, 91%, relative to converted methylal.

100 g of the crude reaction mixture, which contained about 5 g of the ion exchange material used in the carbonylation, were heated for 4 hours under reflux, after 100 g of methanol had been added. In this reaction, the methyl methoxyacetylglycolate originally present was quantitatively converted by alcoholysis into methyl methoxyacetate and methyl glycolate. Fractional distillation of the reaction mixture from which the ion exchange material had been removed by filtration produced 42.5 g of methyl methoxyacetate (boiling point 130° C.) and 13.0 g of methyl glycolate (boiling point 63° C./28 mbar).

EXAMPLE 3

A 200 ml autoclave was filled with 50 g of formaldehyde diethylacetal and 10 g of a perfluorosulfonated polymethylene in H+ form (exchange capacity 1.4 mEq/g). The vessel was flushed with nitrogen, and 225 bar of carbon monoxide were added. The autoclave was heated for 3 hours at 165° C., during which period the carbon monoxide consumed was replenished. After the autoclave had cooled down, the pressure was let down, and the reaction mixture was analyzed by gas chromatography. It contained 38.1% by weight of ethyl glycolate. The conversion of formaldehyde diethylacetal was 72%, and the selectivity to ethyl ethoxyacetate was 45% and to ethyl glycolate 23%.

EXAMPLE 4

A 200 ml shaker autoclave was filled with 50 g of formaldehyde dibutylacetal and 10 g of an ion exchange resin in H+ form (water content 3.5% by weight, exchange capacity 4.3 mEq/g). The further procedure followed was as described in Example 1. The conversion of formaldehyde dibutylacetal was 68% at a selectivity of 48% to butyl butoxyacetate and of 21.3% to butyl glycolate.

We claim:

1. A process for reacting formaldehyde acetals of the formula RO—CH$_2$—OR in which the two R radicals can be identical or different and denote alkyl, alkoxyalkyl, cycloalkyl or phenylalkyl groups having up to 10 carbon atoms at elevated temperatures and pressures with carbon monoxide in the liquid phase, which process comprises using as catalyst acid organic ion exchange materials having an exchange capacity of more than 0.5 mEq per gram.

2. The process as claimed in claim 1, wherein the reaction is carried out at temperatures between 50° and 180° C. and under pressures between 50 and 300 bar.

3. The process as claimed in claim 1 or 2, wherein the reaction is carried out in the presence of organic solvents or diluents.

4. The process as claimed in claim 3, wherein the ion exchange material used has a water content of less than 5% by weight.

5. The process as claimed in claim 4, wherein the reaction mixture formed in the reaction with carbon monoxide is additionally treated with an alcohol.

6. The process as claimed in claim 5, wherein the alcohol used has the formula ROH in which the R radical corresponds to one of the R radicals in the acetal used.

7. The process as claimed in claim 1, wherein the acid organic ion exchange materials have an exchange capacity of more than 1 mEq per gram.

8. The process as claimed in claim 1 wherein the acid organic ion exchange materials have an exchange capacity of more than 1 mEq per gram, the reaction is carried out at temperatures between 50° and 180 ° C. and under pressures between 50 and 250 bar, and the ion exchange material has a water content of less than 5% by weight.

* * * * *